United States Patent

Bond-Thorley

(10) Patent No.: US 9,010,187 B2
(45) Date of Patent: Apr. 21, 2015

(54) SCANNER

(75) Inventor: Andrew Bond-Thorley, Bristol (GB)

(73) Assignee: Airbus Operations Limited, Bristol (GB)

( * ) Notice: Subject to any disclaimer, the term of this patent is extended or adjusted under 35 U.S.C. 154(b) by 775 days.

(21) Appl. No.: 12/922,889

(22) PCT Filed: Apr. 7, 2009

(86) PCT No.: PCT/GB2009/050338
§ 371 (c)(1),
(2), (4) Date: Sep. 16, 2010

(87) PCT Pub. No.: WO2009/127854
PCT Pub. Date: Oct. 22, 2009

(65) Prior Publication Data
US 2011/0013486 A1 Jan. 20, 2011

(30) Foreign Application Priority Data

Apr. 17, 2008 (GB) .................................. 0806997.3

(51) Int. Cl.
| G01N 29/265 | (2006.01) |
| G01N 29/04 | (2006.01) |
| G01N 29/22 | (2006.01) |
| G01N 29/28 | (2006.01) |

(52) U.S. Cl.
CPC .............. *G01N 29/265* (2013.01); *G01N 29/04* (2013.01); *G01N 29/225* (2013.01); *G01N 29/28* (2013.01); *G01N 2291/101* (2013.01); *G01N 2291/2638* (2013.01); *G01N 2291/2694* (2013.01)

(58) Field of Classification Search
USPC ........... 73/639, 633, 634, 635, 636, 637, 638, 73/644, 617, 632, 866.5
See application file for complete search history.

(56) References Cited

U.S. PATENT DOCUMENTS

| 3,257,843 | A | 6/1966 | Cowan |
| 3,423,991 | A | 1/1969 | Collins |
| 3,628,375 | A | 12/1971 | Pagano |
| 4,202,216 | A | 5/1980 | Bull et al. |
| 4,217,782 | A * | 8/1980 | Pont ................................ 73/637 |
| 5,392,652 | A * | 2/1995 | Levesque et al. ............... 73/629 |
| 5,404,755 | A | 4/1995 | Olson |
| 5,576,492 | A | 11/1996 | Phalin |
| 5,719,337 | A | 2/1998 | Hall et al. |
| 6,536,553 | B1 | 3/2003 | Scanlon |

(Continued)

FOREIGN PATENT DOCUMENTS

| GB | 1145134 | 3/1969 |
| JP | 01-129610 | 5/1989 |

(Continued)

OTHER PUBLICATIONS

Search Report for GB0806997.3 mailed Aug. 14, 2008.

(Continued)

*Primary Examiner* — Laura Martin
*Assistant Examiner* — Rose M Miller
(74) *Attorney, Agent, or Firm* — Lowe Hauptman & Ham, LLP (57) ABSTRACT

An ultrasonic scanner has an encoder contacting a drum containing an array. The scanning assembly can be replaced via a snap fit formation. The encoder and drum are resiliently biased and movable relative to the chassis. The array can also be movable relative to the chassis.

19 Claims, 7 Drawing Sheets

(56) References Cited

U.S. PATENT DOCUMENTS 6,604,421 B1 * 8/2003 Li ................................ 73/636
2008/0066553 A1 3/2008 Espada Tejedor

FOREIGN PATENT DOCUMENTS

| JP | 1-129610 U | 9/1989 |
| JP | 03-077056 | 4/1991 |
| JP | 3-77056 A | 4/1991 |
| JP | 04-066865 | 3/1992 |
| JP | 4-66865 A | 3/1992 |
| JP | 06-258294 | 9/1994 |
| JP | 6-258294 A | 9/1994 |
| JP | 11-023544 | 1/1999 |
| JP | 11-23544 A | 1/1999 |
| WO | 82/03920 A1 | 11/1982 |
| WO | 9321523 | 10/1993 |
| WO | 2004025290 | 3/2004 |
| WO | 2005038449 | 4/2005 |

OTHER PUBLICATIONS

Search Report for GB0806997.3 mailed Sep. 11, 2008.
International Search Report for PCT/GB2009/050338 mailed Oct. 30, 2009.
Japanese Office Action for Application No. JP2011-504536 mailed Apr. 16, 2013.
http://www.pts.cz/download/panametrics/en_transducer_catalog.pdf, 31 pages.
Inquiry under the Substantive examination issued in Russian Application No. 2010145060/28(064968), 7 pages.
Office Action issued Feb. 29, 2012 in Chinese Application No. 200910112969.5, 7 pages.
English Translation of Decision of Refusal dated Dec. 17, 2013, in corresponding Japanese Application No. 2011-504536 (2 pages).

* cited by examiner

SCANNER

RELATED APPLICATIONS

The present application is a national phase of PCT/GB2009/050338, filed Apr. 7, 2009, and Great Britain Application Number 0806997.3, filed Apr. 17, 2008.

FIELD OF THE INVENTION

The present invention is concerned with a scanner. More specifically, the present invention is concerned with an ultrasonic testing (UT) scanner for non-destructive testing of metal and composite structures etc.

BACKGROUND OF THE INVENTION

Non-visible areas of materials, such as the interiors of components, welds and composite materials can be analysed using ultrasonic testing. This type of non-destructive testing (NDT) utilises the reflection of sound waves to detect faults and features which would otherwise be very difficult to detect without destroying the component in the process. Ultrasonic testing is a common technique in the aerospace sector to test the integrity of materials at manufacture and during service.

Scanners tend to be of the portable type (i.e. more suited to in-service scanning) or non-portable type (specifically for production).

A feature of ultrasonic testing is that a couplant is required to aid transmission of the ultrasonic energy to the test specimen because the acoustic impedance mismatch between air and solids (i.e. such as the test specimen) is large. This causes reflection of the sound waves and a loss in scan quality if a couplant is not used. Couplants generally take the form of water or gel or a deformable solid.

Traditionally, ultrasonic testing has been limited in terms of inspection speed as the operation had to be carried out on a point-by-point basis. Improvements have led to the development of array scanning, or "paintbrush" scanning which permits a continuous scan over a surface to produce a two dimensional image of the desired region of the test component. Such equipment however is bulky and limited to use in a production (as opposed to service) environment and is not considered portable.

The issue of portability has been addressed with the development of the RapidScan system marketed by NDT Solutions Ltd. This system utilises a chassis to which a water filled rubber drum is rotatably mounted. An ultrasonic array is mounted to the axle and the water contained within the deformable rubber drum acts as the couplant.

The RapidScan system also features a rotary encoder mounted to the chassis proximate the drum. The chassis comprises a handle extending in the direction of travel of the RapidScan system.

In use, the chassis is held by the handle, proximate a workpiece with the drum and encoder contacting said workpiece, and moved such that the drum and encoder rotate. As this occurs, scanning takes place via the array. The scanned signal is fed from the array to a nearby computer for analysis. Simultaneously, the encoder transmits a signal to the computer such that the scanning position and hence the location of any features found can be determined.

There are various problems exhibited by this system. Firstly, the requirement for simultaneous contact of the drum and encoder means that the system cannot easily traverse significant changes in gradient of the workpiece. The device may become "grounded" (i.e. a part of the chassis between the encoder and drum may contact the workpiece). Alternatively, the drum or encoder may part contact with the surface leading to loss of useful results or loss of data relating to the distance travelled.

Also, the orientation of the chassis, and hence handle is fixed relative to the surface of the workpiece and hence the position of the user's hand is constrained in this respect. As such, in workpieces with particularly uneven surfaces, the user has to change the position of their hand relative to their arm/body several times. The various positions may also be uncomfortable to the user.

Also, it is often desirable to use a different frequency ultrasound array. Therefore it is necessary to carry several systems, each with different arrays to provide this functionality.

Further, the drum is mounted directly to the chassis. This limits the speed at which the array can traverse the workpiece as the user has to be careful not to allow the array to leave the workpiece surface at, for example, sharp changes in gradient of the surface or imperfections which the drum may "jump" over. If the drum leaves the workpiece the effect of the couplant is lost and the effectiveness of the scanner is significantly reduced.

Additionally, the stiff mounting arrangement between the drum and the chassis means that all of the force transmitted between the workpiece and the drum is transmitted to the user's hand, which may be uncomfortable in the case of shock or repetitive loading.

It is an aim of the present invention to overcome or at least mitigate at least one of the above problems.

SUMMARY OF THE INVENTION

According to a first aspect of the above invention there is provided a portable scanner comprising: a chassis, a scanning assembly having an ultrasonic scanning array and a rotating component rotatably mounted relative to the chassis, the rotating component comprising an ultrasonic couplant and having a peripheral contact surface for contacting a surface of a workpiece to provide ultrasonic coupling between the array and a surface of a workpiece such that movement of the chassis relative to a workpiece with the contact surface in contact with a surface of a workpiece results in rotation of the rotating component, and an encoder comprising a movement sensor, wherein the sensor is arranged to sense a movement of the rotating component.

In this way, the sensor does not need to have any kind of relationship with the surface of the workpiece which could impair its movement around certain features.

According to a second aspect of the above invention there is provided a portable scanner comprising: a chassis and a scanning assembly having an ultrasonic scanning array and
    a rotating component rotatably mounted relative to the chassis, the rotating component comprising an ultrasonic couplant and having a peripheral contact surface for contacting a surface of a workpiece to provide ultrasonic coupling between the array and a surface of a workpiece such that movement of the chassis relative to a workpiece with the contact surface in contact with a surface of a workpiece results in rotation of the rotating component, and wherein the rotating component is resiliently, translationally moveable relative to the chassis.

As such a form of suspension is provided in which the position of the rotating component is able to adjust to follow variations in the surface without the user needing constantly to adjust the position of their hand holding the scanner.

According to a third aspect of the above invention there is provided a portable scanner comprising: a chassis and a scanning assembly having an ultrasonic scanning array and a rotating component rotatably mounted relative to the chassis, the rotating component comprising an ultrasonic couplant and having a peripheral contact surface for contacting a surface of a workpiece to provide ultrasonic coupling between the array and a surface of a workpiece such that movement of the chassis relative to a workpiece with the contact surface in contact with a surface of a workpiece results in rotation of the rotating component, and wherein; the scanning assembly is removably mounted to the chassis via a quick release formation.

As such, only one scanner chassis is required and scanning assemblies can be easily replaced depending on the requirements of the task.

According to a fourth aspect of the above invention there is provided portable scanner comprising: a chassis and a scanning assembly having an ultrasonic scanning array and a rotating component rotatably mounted relative to the chassis, the rotating component comprising an ultrasonic couplant and having a peripheral contact surface for contacting a surface of a workpiece to provide ultrasonic coupling between the array and a surface of a workpiece such that movement of the chassis relative to a workpiece with the contact surface in contact with a surface of a workpiece results in rotation of the rotating component, and wherein the array is rotatable relative to the chassis.

As such the handle can be moved relative to the array to suit the user's preference for comfort or to use the array in environments where space is limited.

BRIEF DESCRIPTION OF THE DRAWINGS

Embodiments of the invention will now be described with reference to the accompanying drawings in which.

DETAILED DESCRIPTION OF THE EMBODIMENTS

Figure 1A:
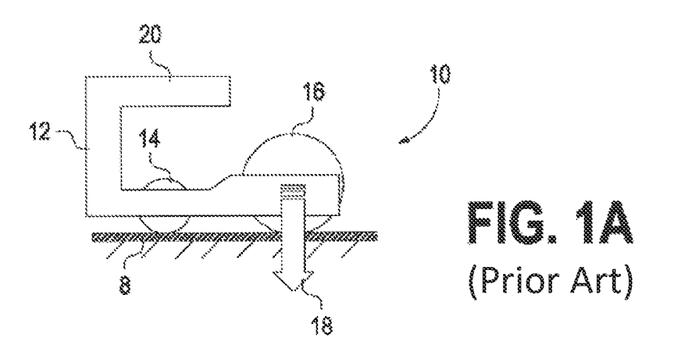
FIG. 1a-1c shows various side views of a prior art scanner in a first position.
Figure 1B:
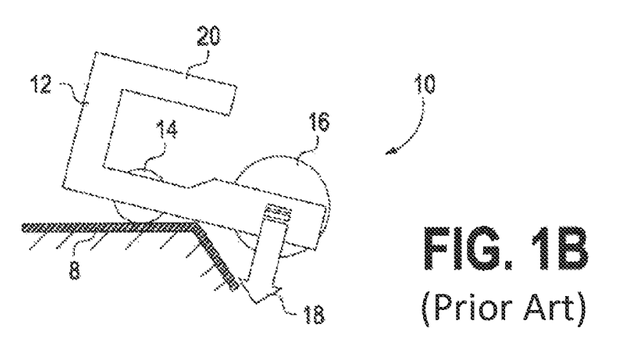
Figure 1C:
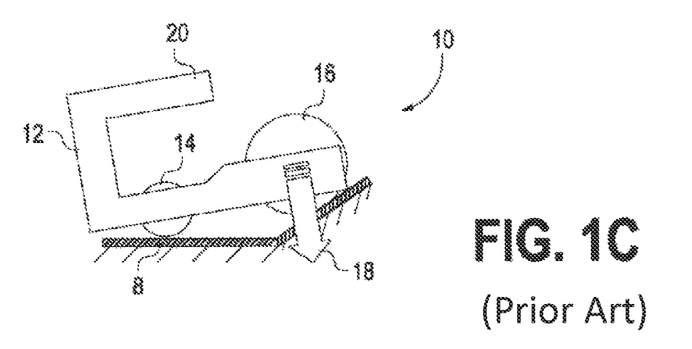

Referring to FIGS. 1a to 1c a prior art scanner 10 is shown schematically and comprises a chassis 12, an encoder wheel 14 and a drum 16. The encoder wheel 14 and the drum 16 both contact a surface of a workpiece 8. The encoder 10 further comprises an array (not shown) located fixed to the chassis 12 and substantially coincident with the axis of rotation of the drum. The array has a scanning direction 18 in which it emits and receives ultrasonic waves to and from the workpiece 8. The scanning direction 18 is fixed relative to the chassis 12. The chassis has a handle 20 by which it may be moved across the workpiece 8 with the encoder wheel 14 and drum 16 rotating relative to the chassis.

In order for the scanner 10 to satisfactorily scan the workpiece 8, the scanning direction 18 should be perpendicular to the surface of the workpiece 8. This occurs in FIG. 1a in which the workpiece 8 has a flat surface.

In FIG. 1b, the scanner has encountered a convex surface of the workpiece 8. In traversing the workpiece 8 the scanner chassis 12 has fouled on it. As such one of the encoder wheel 14 and drum 16 cannot contact the workpiece 8 leading to poor performance. In particular, the scanning direction 18 is not perpendicular to the workpiece 8.

In FIG. 1c the scanner has encountered a concave surface of the workpiece 8. Although both the encoder wheel 14 and the drum 16 are contacting the workpiece, the scanning direction 18 is not perpendicular to it as the encoder wheel 14 restricts rotational movement of the scanner 10. This results in poor performance.

Figures 2A, 2B, 2C:
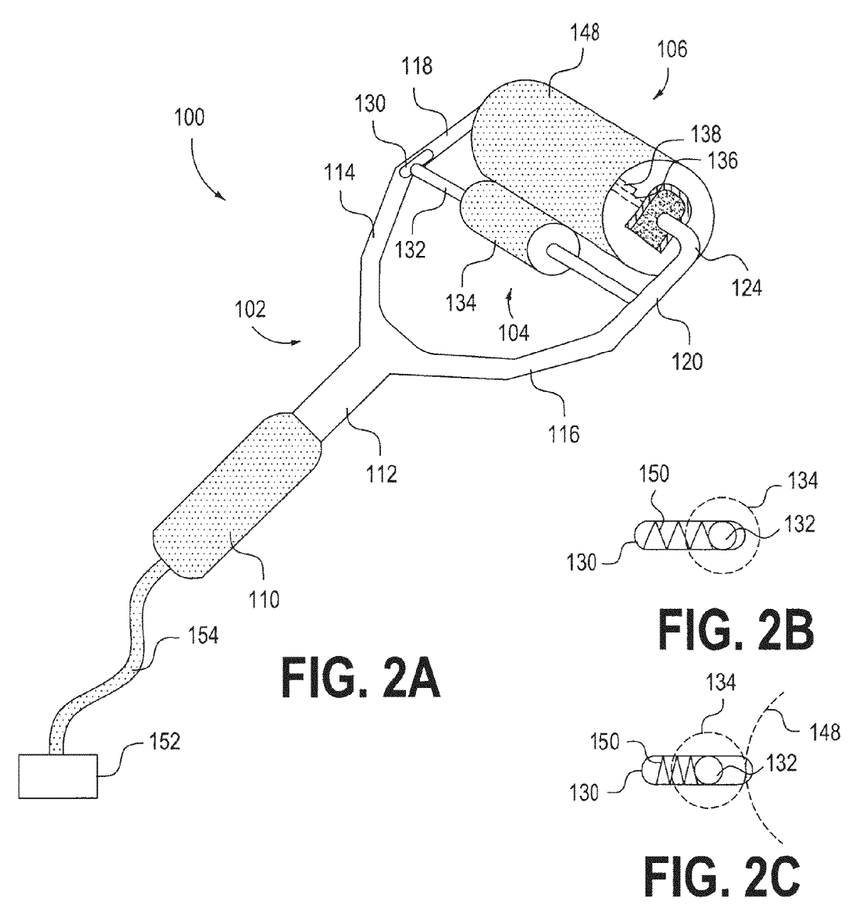
FIG. 2a shows a perspective view of a first embodiment of a scanner in accordance with the present invention.
FIG. 2b shows a schematic view of a part of the scanner of FIG. 1 in a first state.
FIG. 2c shows a schematic view of a part of the scanner of FIG. 1 in a second state.

Referring now to FIG. 2a, a scanner 100 in accordance with the present invention is shown. The scanner 100 comprises a chassis 102, an encoder assembly 104 and a scanning assembly 106.

The chassis 102 comprises an elongate cylindrical handle 110 for a user to grip in his/her hand. The chassis 102 further comprises a frame 112 extending from the handle 110 which splits into two arms 114, 116 to form a "Y" shape. The arms 114, 116 of the "Y" comprise parallel sections 118, 120 respectively. The parallel sections 118, 120 terminate with inwardly depending sections 124 (only one is shown).

Figure 3:
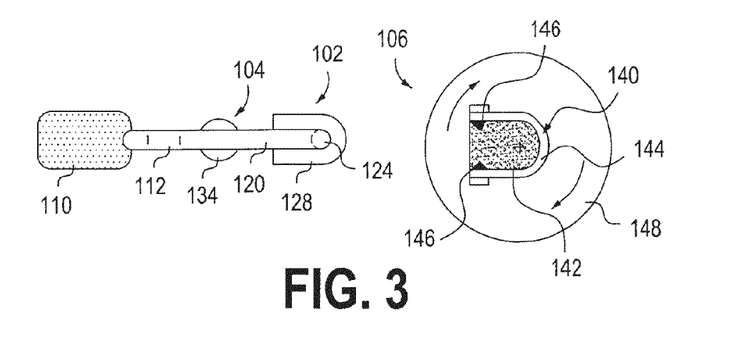
FIG. 3 shows a schematic view of a part of the scanner of FIG. 1.

The inwardly depending sections 124 in turn terminate in clip plates 128 (only one is shown in FIG. 3).

A pair of parallel, facing grooves 130 (only one shown) are formed in the parallel sections 118, 120 whose function will be discussed below.

The encoder assembly 104 comprises a shaft 132 on which an encoder 134 is rotatably mounted. The encoder 134 is of the rotary type and is configured to determine the distance travelled over the surface in which it is in contact.

The scanning assembly 106 comprises an axle 136 onto which an ultrasonic scanning array 138 is mounted. At either end of the axle 136 there are positioned clip receiving assemblies 140 (only one shown in FIG. 3) which comprise (with reference to FIG. 3) a base plate 142, a channel section rim 144 and resiliently mounted retaining pins 146.

The scanning assembly further comprises a drum 148 having a rubber body containing water to act as a couplant for the array 138. The drum 148 is rotatably mounted to the axle 136 such that it can rotate relative to the array 138.

The encoder assembly 104 is mounted to the chassis 102 by inserting the ends of the shaft 132 into the grooves 130. Springs 150 (only one shown in FIG. 2B) are also inserted into the grooves 130 to bias the shaft 132 away from the handle 110 of the chassis 102.

The scanning assembly 106 can then be assembled to the chassis 102 by inserting the clip plates 128 into the clip receiving assemblies 140. As this is performed, the retaining pins 146 are urged outwards to allow the clip plates 128 to pass. Once the clip plates 128 are securely within the clip receiving assemblies the retaining pins resile to their original positions to retain the scanning assembly in position.

Whilst the scanning assembly is being assembled to the chassis 102 as described above, the drum 148 contacts the encoder 134 and moves it against the bias of the springs 150. When in position, the drum 148 is therefore reliably contacted by the encoder 134.

Both the array 138 and the encoder 134 are connected to a computer 152 for collecting information regarding the scanning results (via the array 138) and the position of the scanner (via the encoder 134). The encoder and scanner have signal feed wires (not shown) which connect to a main cable 154 which leads from the handle 110 to the computer 152.

Figure 4A:
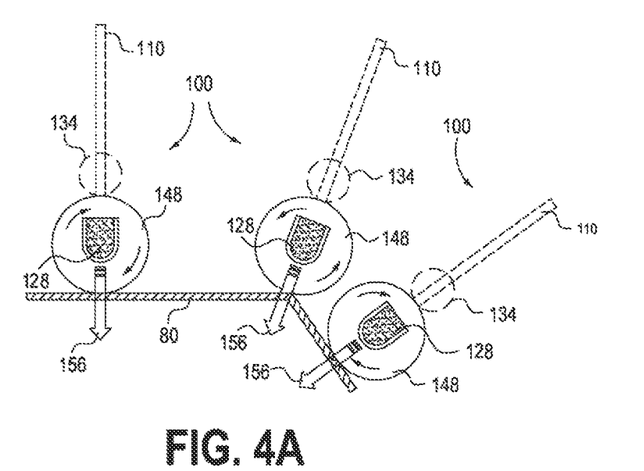
FIG. 4a shows a schematic view of the scanner of FIG. 1 in use.

Referring to FIG. 4a the scanner 100 is shown traversing a workpiece 80 similar to that shown in FIG. 1b. The scanner 100 is held by a user (not shown) with the handle 110 perpendicular to the surface of the workpiece 80. The array 138 scans the workpiece 80 by sending and receiving ultrasonic waves in a scanning direction 156. When moving over the corner of the workpiece, the handle 110 can be manoeuvred by the user to remain perpendicular to the surface, thus maintaining a perpendicular scanning direction 156 as shown.

As can be observed, the ability to keep the scanning direction 156 perpendicular to the surface is enabled by the single contact point (or line) between the drum 148 and the workpiece 80. As the encoder 134 determines the distance travelled by the drum 148 there is no need for it to contact the workpiece 80 and as such the problems observed in FIGS. 1b and 1c do not occur.

Figure 4B:
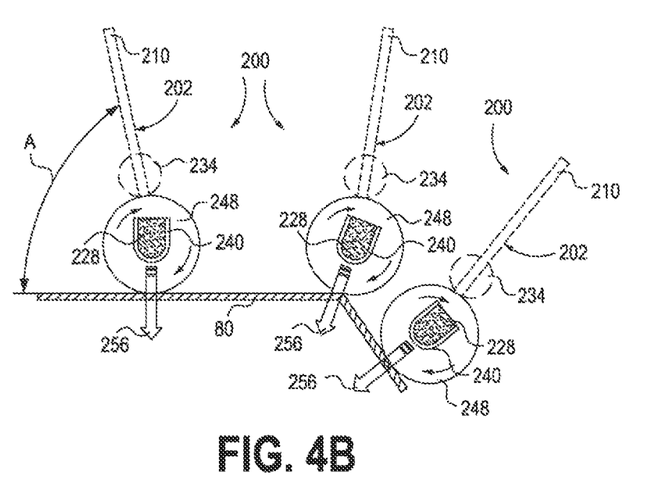
FIG. 4b shows a schematic view of a second embodiment of a scanner in use.

Scanner 100 in FIG. 4a shows the array 138 arranged with its scanning direction 156 parallel to the handle 110. It is envisaged that the array may be arranged at an angle to the handle 110. An example of this is shown in FIG. 4b where an scanner 200 has features numbered as scanner 100, but 100 greater.

The scanner 200 is similar to the scanner 100 except that the clip plates 228 are mounted at an angle to the chassis 202 and hence handle 210. Therefore in order to maintain the scanning direction 256 parallel to the workpiece 80 the handle 210 needs to be positioned at an angle A relative thereto. An arrow or sign may be provided on the clip plate outer to inform the user of the required scanning direction 256.

This arrangement may be more comfortable for the user than when the handle is perpendicular to the surface (i.e. when A=90 degrees).

The clip plates 228 may be adjustably mounted to the chassis 202 to provide user adjustment capability which may be varied depending on the user's comfort levels and space available for scanning.

Alternatively, the clip receiving assemblies may be oriented as per scanner 100, and the array may be angled with respect to the clip receiving assemblies 140. As such the angle A would be dependent on the choice of scanning assembly 106.

Figures 5, 6:
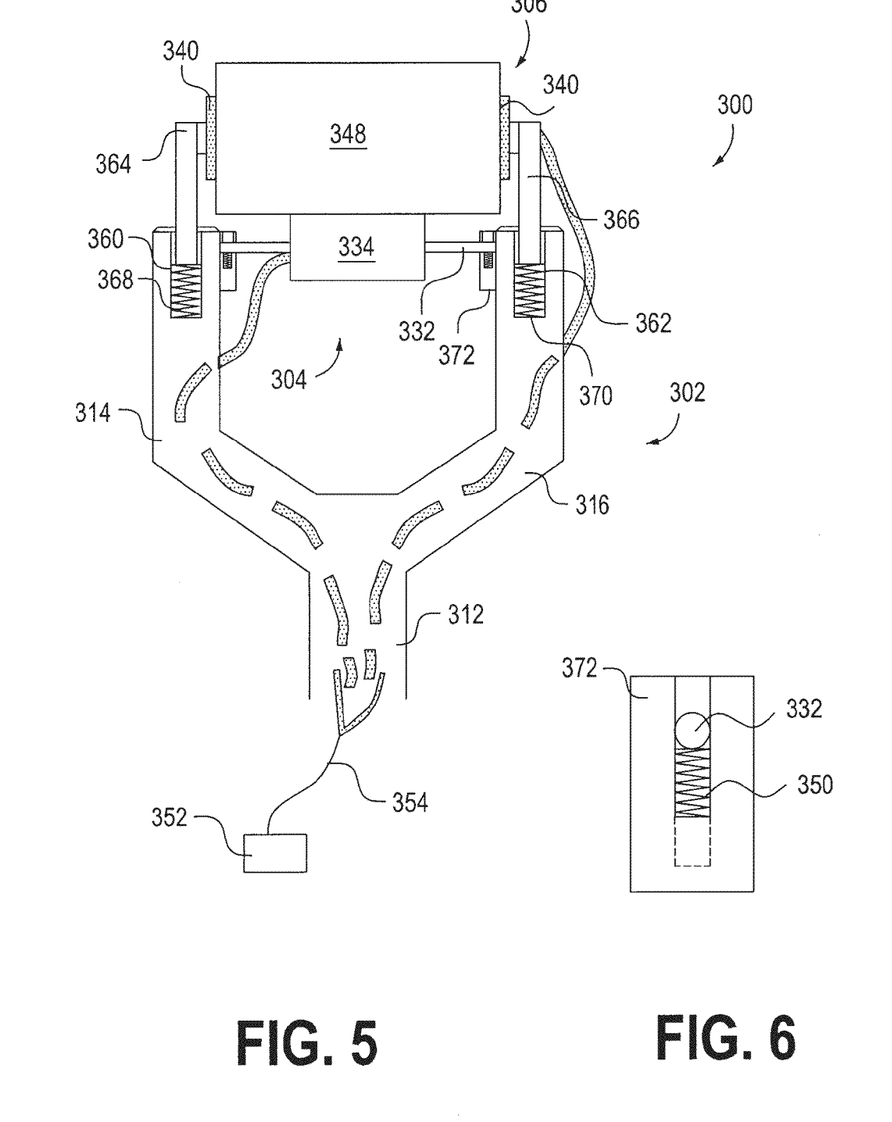
FIG. 5 shows a top partial section view of a third embodiment of a scanner in accordance with the present invention.
FIG. 6 shows a schematic view of a part of the scanner of FIG. 5, FIGS. 7a-7c show a schematic side view of the scanner of FIG. 5 in use.

Referring to FIG. 5, a scanner 300 is shown which is similar to the scanner 100. Common features are numbered 200 greater. In place of parallel sections 118, 120, the arms 314, 316 of the frame 312 of the chassis 302 comprise longitudinal bores 360, 362 respectively. A pair of pistons 364, 366 are located in the respective bores 360,362 and are biased to an extended position via springs 368, 370.

The pistons 364, 366 can move axially with respect to the frame 312.

Each of the pistons 364, 366 has a clip plate (not shown) mounted thereto which is engaged with the clip retaining formations 340 of the scanning assembly 306 as described above.

The encoder assembly 304 is also resiliently mounted to be biased towards the scanning assembly 306 as per scanner 100. However, due to the location of the above piston arrangement the encoder assembly is resiliently mounted with the shaft 332 movable in slots 330 in additional lugs 372 and biased with spring 350 (see FIG. 6).

In use, the scanning assembly 306 of the scanner 300 is therefore resiliently movably mounted to the chassis 302. During use, movement of the drum 348 is accompanied by movement of the encoder assembly 304 such that the drum 348 and encoder 334 are always in contact.

Figure 7A:
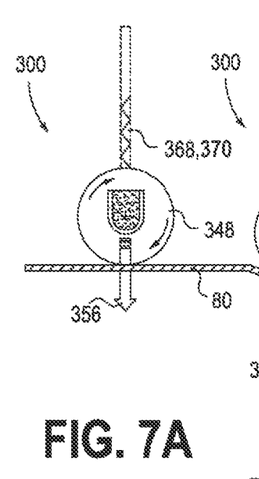
Figures 7B, 7C:
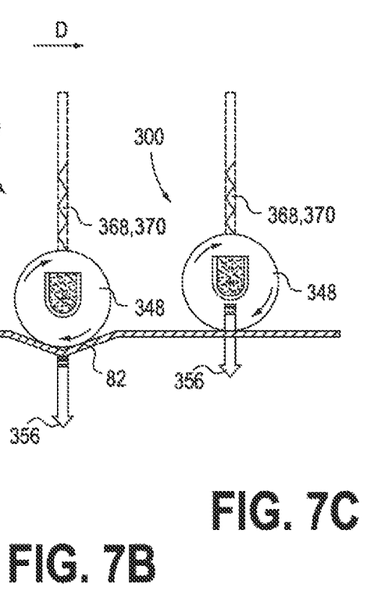

Referring to FIGS. 7a-7c, the scanner 300 is propelled along a surface of a workpiece 80 in a direction D by the user. The surface contains an imperfection or concave feature 82 which the scanner 300 has to traverse. The user is applying a light pressure in the scanning direction 356. The springs 368, 370 are schematically represented as lightly compressed.

When the scanner encounters the feature 82 the springs 368, 370 are able to extend to allow the drum 348 to remain in contact with the workpiece 80. As such, contact is not lost and the scan may be completed successfully.

Figures 8A, 8B:
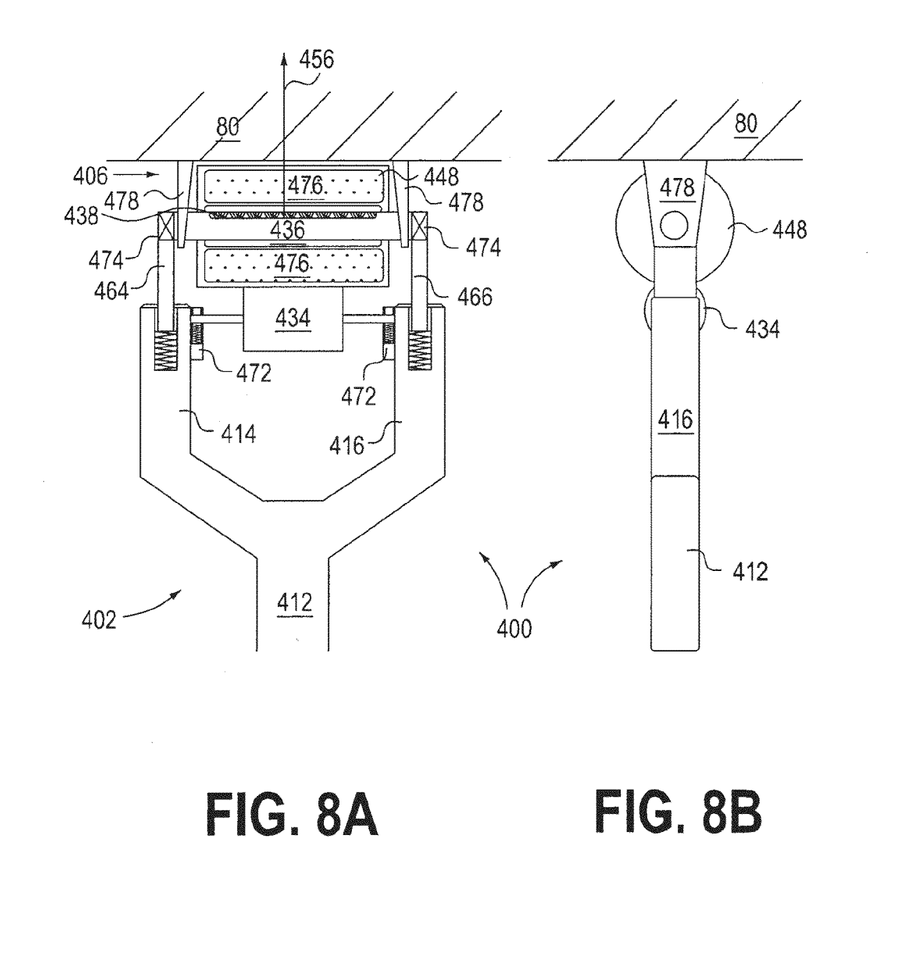
FIG. 8a shows a partially sectioned front view of a third embodiment of a scanner in accordance with the present invention.
FIG. 8b shows a side view of the scanner of FIG. 8a, and FIGS. 9a-9c show schematic views of the hand scanner of FIG. 8a in a variety of configurations.

Turning to FIGS. 8a and 8b a scanner 400 is shown substantially similar to the hand scanner 300 with common features numbered 100 greater.

In the case of scanner 400, the axle 436 is mounted to the arms 414, 416 of the frame 412 of the chassis 402 via tilt bearings 474 such that the axle 436 may rotate relative to the frame 412. The array 438 is mounted to the axle to scan in the scanning direction 456.

The drum 448 of the scanning assembly 406 is rotationally mounted relative to the axle 436 as in previous embodiments. The drum 448 is shown in section with water filled bladder 476 acting as the couplant.

Two stabilisers 478 are attached to the axle 436 where it protrudes from the drum 448 and extend radially therefrom. The stabilisers extend approximately to the outer perimeter of the drum 448.

In use, the outer periphery of the drum 448 contacts the workpiece 80 and can roll on it as previously described. In scanner 400 however, the stabilisers 478 prevent rotation of the axle 436 with respect to the surface of the workpiece 80 as they run over it. As such, the array 438 is orientated such that the scanning direction 456 is always perpendicular to the surface of the workpiece 80.

Additionally, the frame 412 may be rotated with respect to the scanning assembly 406 without moving the position of the array 438 by virtue of the tilt bearings 474. Accordingly, the user can continuously adjust his/her hand position if desired to achieve a greater comfort level or use the scanner 400 in confined spaces.

Figure 9A:
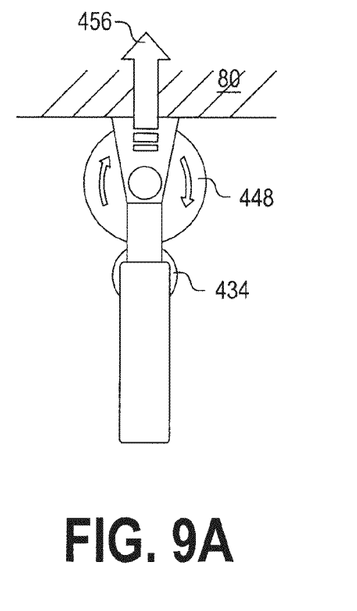
Figure 9B:
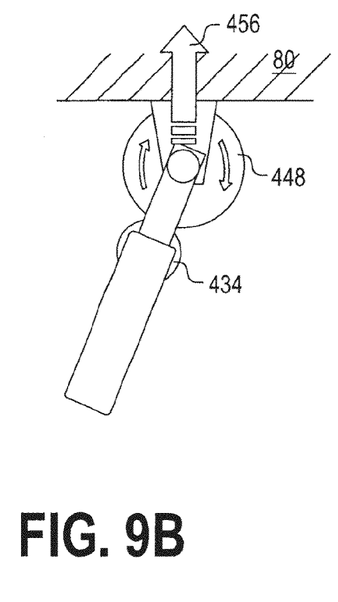
Figure 9C:
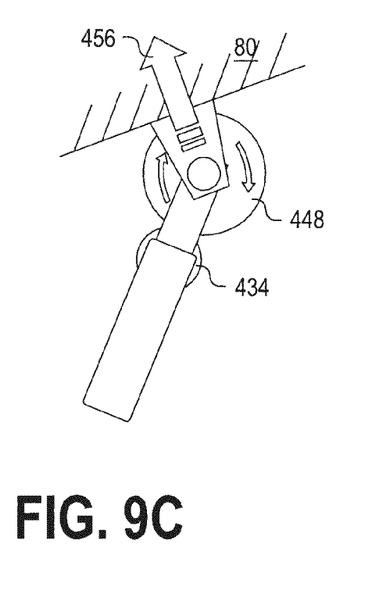

Turning to FIGS. 9a to 9c, the scanner 400 is shown in a variety of positions with the drum 448 and the stabilisers 478 contacting the workpiece 80. As shown in FIGS. 9b and 9c, the angle of the surface and/or the angle of the handle of the device can be altered without affecting the scanning direction's perpendicularity to the surface of the workpiece 80.

Many variations of the embodiments described fall within the scope of the present invention.

For example, the use of the encoder contacting the drum, the resiliently mounted drum, the snap fit and the stabilisers may be used alone or in any suitable combination depending on the application.

The improvements described above may be applied to a non-portable (production type) scanner as well as a portable (in-service) scanner as discussed.

The snap fit connection may be any quick release formation such as recessed sprung pins, quarter turn bolts/screws, butterfly nuts and the like.

The encoder may be of any type, for example a mechanical device as discussed above, or an optical device which reads the surface of the drum without contact.

The drum may take any form and need not be water filled to achieve coupling, for example deformable solids or gels may be appropriate.

The array and encoder may not be connected to the computer via a wired connection, but may be wireless.

The connection between the array and the computer may be achieved via a contact connection within the mounting point of the scanning assembly and the frame—for example the frame may have exposed connections on the clip plate and the scanning assembly may have corresponding connections on the clip receiving assemblies.

The device may only comprise a single stabiliser.

Various figures depict an encoder 234, an array 238, a clip receiving assembly 240, a drum 248 and an encoder 434. As detailed above, encoder 200 has features numbered as encoder 100, but 100 greater, scanner 300 is shown which is similar to the scanner 100, where common features are numbered 200 greater, and scanner 400 is shown substantially similar to the hand scanner 300 with common features numbered 100 greater.

The invention claimed is:

1. A scanner comprising:
   a chassis,
   a scanning assembly having an ultrasonic scanning array having a scanning direction, the scanning assembly having a rotating component rotatably mounted relative to the chassis, the rotating component comprising an ultrasonic couplant and having a peripheral contact surface for contacting a surface of a workpiece to provide ultrasonic coupling between the array and a surface of a workpiece such that movement of the chassis relative to a workpiece with the contact surface in contact with a surface of a workpiece results in rotation of the rotating component with the array orientated to keep the scanning direction perpendicular to the surface, and
   an encoder comprising a movement sensor, wherein;
   the sensor is arranged to sense a movement of the rotating component, and
   in which the array is rotationally adjustable relative to the chassis to provide a selectable fixed chassis position in use.

2. A scanner according to claim 1 in which the movement sensor contacts the rotating component.

3. A scanner according to claim 2 in which the movement sensor is a rotary component of a rotary encoder.

4. A scanner according to claim which the movement sensor is movably mounted to the chassis and resiliently biased towards the rotating component.

5. A scanner according to claim 1 in which the movement sensor contacts the peripheral contact surface of the rotating component.

6. A scanner according to claim 1 in which the rotating component is resiliently, translationally moveable relative to the chassis.

7. A scanner according to claim 1 in which the scanning assembly is removably mounted to the chassis via a quick release formation.

8. A scanner according to claim 1, wherein the scanner is a hand held scanner.

9. A scanner according to claim 1, wherein the scanner includes an apparatus configured to enable the array to be rotationally adjustable relative to the chassis to provide a selectable fixed chassis position in use.

10. A scanner according to claim 1, wherein the scanner includes means for the array to be rotationally adjustable relative to the chassis to provide a selectable fixed chassis position in use.

11. A scanner according to claim 1, wherein the array is mounted to an axle, and the axle is rotationally adjustably mounted to the chassis to provide a selectable fixed chassis position in use.

12. A scanner according to claim 1, wherein the scanner includes an axle that enables the array to rotate relative to the chassis to provide a selectable fixed chassis position in use.

13. A scanner comprising:
   a chassis and
   a scanning assembly having an ultrasonic scanning array and a rotating component rotatably mounted relative to the chassis, the rotating component comprising an ultrasonic couplant and having a peripheral contact surface for contacting a surface of a workpiece to provide ultrasonic coupling between the array and a surface of a workpiece such that movement of the chassis relative to a workpiece with the contact surface in contact with a surface of a workpiece results in rotation of the rotating component, wherein;
   the rotating component is resiliently, translationally moveable relative to the chassis, and
   the scanner comprises an encoder having a movement sensor, wherein the sensor is arranged to sense a movement of the rotating component by contact with the rotating component, the movement sensor being movably mounted to the chassis and resiliently biased towards the rotating component.

14. A scanner according to claim 13 in which the rotating component is resiliently and translationally mounted to the chassis via an axle of the rotating component.

15. A scanner according to claim 14 in which the axle is resiliently and translationally mounted to the chassis at two spaced apart positions.

16. A scanner according to claim 15 in which the positions span the rotating component.

17. A scanner according to claim 13, wherein the scanner is a hand held scanner.

18. A scanner according to claim 13, wherein the array is rotationally adjustable relative to the chassis to provide a selectable fixed chassis position in use.

19. A scanner according to claim 13, wherein the array is rotationally adjustable relative to the chassis so as to enable a plurality of chassis positions in use.

* * * * *